United States Patent
Delaunay et al.

(10) Patent No.: US 10,646,601 B2
(45) Date of Patent: May 12, 2020

(54) DEVICE AND METHOD FOR TRANSFERRING A STERILE PRODUCT BETWEEN TWO CONTAINERS

(71) Applicant: PIERRE FABRE DERMO-COSMETIQUE, Boulogne (FR)

(72) Inventors: Jean-Claude Delaunay, Clermont l'Herault (FR); Laurent Serra, La Tour sur Orb (FR)

(73) Assignee: PIERRE FABRE DERMO-COSMETIQUE, Boulogne (FR)

( * ) Notice: Subject to any disclaimer, the term of this patent is extended or adjusted under 35 U.S.C. 154(b) by 0 days.

(21) Appl. No.: 15/110,738

(22) PCT Filed: Jan. 22, 2015

(86) PCT No.: PCT/EP2015/051256
§ 371 (c)(1),
(2) Date: Jul. 9, 2016

(87) PCT Pub. No.: WO2015/110531
PCT Pub. Date: Jul. 30, 2015

(65) Prior Publication Data
US 2016/0324995 A1    Nov. 10, 2016

(30) Foreign Application Priority Data

Jan. 24, 2014 (FR) ..................... 14 50604

(51) Int. Cl.
*A61L 2/07* (2006.01)
*A61L 2/00* (2006.01)

(52) U.S. Cl.
CPC ............... *A61L 2/07* (2013.01); *A61L 2/0023* (2013.01); *A61L 2202/121* (2013.01);
(Continued)

(58) Field of Classification Search
CPC .... A61L 2/07; A61L 2/0023; A61L 2202/123; A61L 2202/18; A61L 2202/21; A61L 2207/121
(Continued)

(56) References Cited

U.S. PATENT DOCUMENTS

| 300,113 | A | * | 6/1884 | Nibaelius | .................. | A61L 2/07 |
| | | | | | | 422/295 |
| 572,779 | A | * | 12/1896 | Theurer | ................ | B05C 5/0225 |
| | | | | | | 222/1 |

(Continued)

FOREIGN PATENT DOCUMENTS

| CN | 201660307 U | 12/2010 | |
| DE | 102012108526 A1 | * 3/2014 | ........... B67C 3/2608 |

(Continued)

*Primary Examiner* — Timothy L Maust
*Assistant Examiner* — James R Hakomaki
(74) *Attorney, Agent, or Firm* — Im IP Law; Chai Im; C. Andrew Im (57) ABSTRACT

A device for transferring a sterile product from one container to another under aseptic conditions. The first container to initially contain the sterile product and equipped with an outlet. The outlet has a first pipe and two independently operable valves mounted in series thereon. The second container is equipped with an inlet having a second pipe and two independently operable valves mounted in series thereon. A removable hose to provide a sealed connection of the free end of the first pipe and the free end of the second pipe. A connector to connect the removable hose to a system for sterilizing the internal volume thereof. The system is operable when the removable hose connects the free end of the first pipe with the free end of the second pipe in a sealed manner.

17 Claims, 3 Drawing Sheets

(52) U.S. Cl.
CPC ..... *A61L 2202/123* (2013.01); *A61L 2202/18* (2013.01); *A61L 2202/21* (2013.01)

(58) Field of Classification Search
USPC .......... 141/18, 287, 285, 329; 134/18, 115 R
See application file for complete search history.

(56) References Cited

U.S. PATENT DOCUMENTS

| | | | | |
|---|---|---|---|---|
| 704,182 | A * | 7/1902 | Francis | A61L 2/07 422/295 |
| 1,714,597 | A * | 5/1929 | Grindrod | A23C 3/031 426/580 |
| 2,175,951 | A * | 10/1939 | Bulleri | B08B 9/0323 137/239 |
| 2,219,772 | A * | 10/1940 | Gernhardt | A23B 4/015 426/244 |
| 2,297,190 | A * | 9/1942 | McKinnis | A23L 2/44 141/234 |
| 2,395,932 | A * | 3/1946 | Levin | B67D 1/04 62/390 |
| 2,689,818 | A * | 9/1954 | Fischer | C12C 11/00 435/252.1 |
| 3,359,062 | A * | 12/1967 | Palm | B65B 55/02 134/30 |
| 3,481,109 | A * | 12/1969 | Pavey | B65B 55/04 141/85 |
| 3,827,455 | A * | 8/1974 | Lee | B65D 90/503 137/264 |
| 4,360,435 | A * | 11/1982 | Bellamy | A61L 2/022 210/636 |
| 4,915,689 | A * | 4/1990 | Theeuwes | A61M 5/1409 137/3 |
| 4,926,913 | A * | 5/1990 | Palm | G01N 1/10 141/1 |
| 5,046,320 | A * | 9/1991 | Loose | F25B 41/003 62/292 |
| 5,118,471 | A * | 6/1992 | Andersen | A61L 2/206 422/1 |
| 5,269,350 | A * | 12/1993 | Galloway | B67B 7/26 141/1 |
| 5,562,130 | A * | 10/1996 | Peha | B64G 1/402 137/205 |
| 5,628,895 | A * | 5/1997 | Zucholl | C02F 1/325 210/143 |
| 5,810,040 | A * | 9/1998 | Ludwig | B65D 88/54 137/312 |
| 5,876,511 | A * | 3/1999 | Till | B08B 9/08 134/10 |
| 6,308,753 | B1 * | 10/2001 | Nimberger | B67D 7/3218 137/1 |
| 6,357,488 | B1 | 3/2002 | Brossard et al. | |
| 6,528,017 | B2 * | 3/2003 | Jacobs | A61L 2/14 422/300 |
| 6,722,405 | B2 * | 4/2004 | Cessac | F16K 17/20 137/614.04 |
| 7,294,305 | B2 * | 11/2007 | Lin | A61L 2/14 422/300 |
| 7,803,316 | B2 * | 9/2010 | Lin | A61L 2/208 134/22.12 |
| 2004/0028555 | A1 * | 2/2004 | Warburton-Pitt | A61L 2/07 422/26 |
| 2004/0042943 | A1 * | 3/2004 | Wanselin | A61L 2/07 422/295 |
| 2007/0283667 | A1 * | 12/2007 | Kristiansson | B65B 55/08 53/426 |
| 2008/0236621 | A1 * | 10/2008 | Lin | A61L 2/07 134/18 |
| 2010/0084045 | A1 * | 4/2010 | Adams | A61L 2/07 141/11 |
| 2010/0111760 | A1 * | 5/2010 | Ringstrom | A23C 7/02 422/38 |
| 2011/0265820 | A1 * | 11/2011 | Dahlberg | B08B 9/0321 134/10 |
| 2013/0195717 | A1 * | 8/2013 | Fehr | A61L 2/208 422/28 |
| 2014/0316332 | A1 * | 10/2014 | Lo | A61M 1/1656 604/28 |
| 2015/0129041 | A1 * | 5/2015 | Stowers | F17D 1/02 137/1 |
| 2016/0346414 | A1 * | 12/2016 | De Stoutz | A23L 3/16 |

FOREIGN PATENT DOCUMENTS

| | | |
|---|---|---|
| EP | 1 067 089 A1 | 1/2001 |
| EP | 1 260 235 A1 | 11/2002 |
| GB | 2 398 244 A | 8/2004 |
| JP | 61282064 A * | 12/1986 |
| JP | H2195866 A * | 8/1990 |
| JP | H05 49683 A | 3/1993 |
| JP | H549683 A * | 3/1993 |
| JP | 2001-055207 A | 2/2001 |
| WO | 91/11203 A1 | 8/1991 |
| WO | 00/74735 A1 | 12/2000 |
| WO | 02/080990 A1 | 10/2002 |
| WO | 2009/045713 A2 | 4/2009 |

* cited by examiner

DEVICE AND METHOD FOR TRANSFERRING A STERILE PRODUCT BETWEEN TWO CONTAINERS

RELATED APPLICATIONS

This application is a § 371 application from PCT/EP2015/051256 filed Jan. 22, 2015, which claims priority from French Patent Application No. 14 50604 filed Jan. 24, 2014, each of which is incorporated herein by reference in its entirety.

FIELD OF THE INVENTION

The present invention relates to a device for transferring in aseptic conditions a sterile product, in particular a fluid product, from a first container into a second container, as well as to a transfer method which implements such a device.

The invention has an application in particular in lines for production and/or packaging of sterile products in the pharmaceuticals, cosmetics, in particular dermo-cosmetics, veterinary or agro-foodstuffs fields. These products can be both in fluid form, for example in the form of a gel, cream or milk, and more generally in the form of solutions or suspensions, and in powder form. They can in particular be injectable drugs, eye lotions and ophthalmic ointments, parenteral nutrition products, topical cosmetic compositions, etc. The containers between which the sterile products must be transferred can be of any type, for example vessel to vessel, vessel to filler, etc.

BACKGROUND OF THE INVENTION

In such fields, the products must comply with stringent preservation standards in relation to the proliferation of microbes. One of the methods for ensuring this preservation is to include preservation agents in the product. However, these preservation agents may be badly tolerated by the user, and it is preferable to propose products which do not contain additives of this type, but which nevertheless have an adequate preservation period and microbial cleanliness. This objective can be achieved by sterilization of the products, and preservation of them in conditions which can maintain this sterility.

The sterility of a product is defined here in a manner which in itself is conventional, according to standard EN 556 and the European pharmacopeia in force, as the probability of a microorganism proliferating in the product. Typically, this probability is less than $10^{-6}$. According to standard ISO 13408 concerning the sterile production of health products, the sterile product must have been treated by means of a sterilization method, the sterilization value F0 of which must be more than 15 minutes. This value F0, the method for determination of which is defined by the European pharmacopeia in force, gives a time expressed in minutes which quantifies the lethal effect of humid heat at 121° C. on viable microorganisms. A product which is sterile according to the European pharmacopeia has been subjected to a sterilization process, the sterilization value F0 of which is equal to at least 15 minutes.

During their production or packaging, sterile products frequently have to be transferred from a first sterile container which contains them, into a second container which is also sterile, in particular for their temporary storage, or in order to distribute them between different packaging lines. It is then essential for transfer of this type to take place in conditions which make it possible to maintain the sterility of the product during its path from the first container to the second container.

Conventionally, the means which are used for transfer of this type consist of isolators provided with special doors, known as STDDs (Sealed Transfer Door Devices), such as the one described in patent application EP 1 067 089. These devices require an environment which is controlled and monitored from the microbiological point of view, and the transfer is thus implemented in a sealed enclosure, the internal atmosphere of which is kept sterile, thus involving in particular renewal of its internal air volume and absolute filtering. Such a transfer process in aseptic conditions is lengthy and demanding to implement, since it requires in particular application of considerable precautions in order to ensure that adequate sterile conditions are maintained in the enclosure, such that nothing is introduced which can constitute a source of microbial contamination of the product during its transfer from one container to the other. The cost of purchasing systems of this type, and the costs of consumables, are also high.

Aseptic connectors for application to sterile solutions which do not require a controlled environment have also been proposed in the prior art. However, these connectors do not permit transfer of fluid products of all types, in particular viscous products, with a high flow rate of more than 15 kg/hour. They are therefore not at all suitable for a context of industrial production and packaging of large quantities of sterile products. Finally, they are single-use.

OBJECT AND SUMMARY OF THE INVENTION

The present invention aims at eliminating the disadvantages of the devices and methods for transferring a sterile product, in particular of a fluid cosmetic or pharmaceutical product, from a first container to another container, as proposed by the prior art, and in particular the above-described disadvantages, by proposing such a device and a method which implements it, which make it possible to carry out such a transfer in aseptic conditions, easily and rapidly, including in a non-sterile environment, and irrespective of the characteristics of the product to be transferred, in particular its viscosity. An objective of the invention is also for this device to be reusable after cleaning and sterilization, and for it to be able to ensure transfer of the product with high flow rates.

For this purpose, according to the present invention, a device is proposed for transferring a sterile product in aseptic conditions from a first container into a second container, this device comprising:

a first container which is intended to contain the sterile product, which is equipped, preferably in its low part, with emptying means comprising a first pipe on which there are fitted in series two opening/closure valves which can be operated independently from one another, comprising a first valve, called the proximal valve, arranged on the first container side, and a second valve, called the distal valve, arranged on the side of an opposite free end of the first pipe;

a second container which is equipped, preferably in its low part, with filling means comprising a second pipe on which there is fitted an opening/closure valve, preferably on which there are fitted in series two opening/closure valves which can be operated independently from one another, comprising a first valve, called the proximal valve, arranged on the second container side, and a second valve, called the distal valve, arranged on the side of an opposite free end of the second pipe;

a removable hose for sealed connection of the free end of the first pipe and the free end of the second pipe; and means for connection of the removable hose to a system for sterilization of its inner volume, which can be operated when the removable hose connects the free end of the first pipe and the free end of the second pipe in a sealed manner.

According to the invention, a method for transferring, in aseptic conditions, a sterile product from the first container into the second container of the device according to the invention comprises the successive steps of:

a) filling the first container with the sterile product, in a configuration in which at least one valve associated with the first container, and preferably the proximal valve, is closed;

b) sealed connection by the removable hose of the free end of the first pipe and of the free end of the second pipe;

c) connection of the removable hose to a system for sterilization of its inner volume;

d) sterilization of the inner volume of the removable hose;

e) disconnection of the removable hose and of the system for sterilization of its inner volume;

f) opening of all of the valves associated respectively with the first container and the second container;

g) transferring the sterile product from the first container into the second container, via the removable hose; and h) closure of at least one valve associated with the second container.

Such a device and its method for implementation advantageously make it possible to transfer the sterile product from the first container into the second container in aseptic conditions, irrespective of the environment in which the containers are located, including in environments with uncontrolled microbiological conditions. In the present description, aseptic conditions mean conditions which do not generate microbiological contamination of the product transferred, i.e. which cannot degrade the microbiological quality by external contamination.

The method according to the invention is also faster and less demanding to implement than the methods proposed by the prior art. Indeed, whereas in the prior art, in order to implement the transfer of the sterile product from one container to the other, the sterility of the environment outside the containers must be maintained continually, and in particular the sterility of the means for transfer of the product between the containers, with this maintenance requiring numerous specific and delicate operations, the present invention contrarily involves temporary interruption of the sterility, and implementation of a removable hose which is initially not sterile. This removable hose is connected to the pipes which are associated respectively with the first container and with the second container, without interruption of the sterility in the containers and in the parts of the pipes which are respectively adjacent to them, then the hose is advantageously sterilized in situ, in order to recreate a sterile environment along the entire path to be followed by the sterile product, for its transfer from the first container to the second container. This advantageously results in a saving of time, associated with the absence of environmental microbiological control constraints.

The device and the transfer method according to the invention are particularly useful in contexts where it is necessary to displace containers containing a sterile product, for example in order to divide up a batch of sterile products produced so as to adapt to particular packaging requirements, or to move the sterile product from a production factory to a packaging factory.

According to particular embodiments, the invention also complies with the following characteristics, implemented separately or in each of their technically operative combinations.

The step d) of sterilization of the inner volume of the removable hose can be carried out by means of any method which is known in itself. In particular embodiments of the invention, it is carried out by pressurized clean steam, using a conventional sterilization system, such as a clean steam generator device which frequently equips sites for production and packaging of sterile products.

Before this step of sterilization of the inner volume of the removable hose, the method according to the invention advantageously includes a step of checking the state of the proximal valve and the distal valve associated with the first container, and a step of closure of that of said valves which may not be closed. This step is in particular highly advantageously in particular embodiments of the invention in which, during the step a) of filling of the first container by the sterile product, the proximal valve associated with the first container is already closed. Indeed, in the part of the first pipe which is situated between the proximal valve and the distal valve, a sterile empty volume is then formed, which, during the sterilization of the removable hose, isolates the product contained in the first container against the heat of the steam used for the sterilization of the removable hose. This is particularly advantageous in particular when the product contains one or more heat-sensitive components.

In particular embodiments of the invention, the first container comprises, preferably in the high part, a means for sealed connection to a system for sterilization of its inner volume. This means for sealed connection to a sterilization system is preferably distinct from the first pipe, which forms part of the means for emptying the first container. The first container can also comprise, preferably also in the high part, a means for sealed connection to a hose for filling with the sterile product, which is also preferably distinct from the first pipe. This means for sealed connection to a filling hose preferably coincides with the means for sealed connection to the system for sterilization of the inner volume of the first container.

The second container can also comprise, preferably in the high part, a means for sealed connection to a system for sterilization of its inner volume. This means for sealed connection to a sterilization system is preferably distinct from the second pipe, which forms part of the means for filling the second container.

Such features advantageously make it possible to sterilize the inner volumes of the first container and/or of the second container in situ, in particular by means of a pressurized clean steam sterilization system, for example a clean steam generator device which in itself is conventional. Such a pressurized clean steam sterilization system is preferably the same as the one implemented for sterilization of the inner volume of the removable hose.

Highly advantageously, when the method according to the invention comprises a step of sterilization of the inner volume of the first container and/or a step of sterilization of the inner volume of the second container, carried out by pressurized clean steam, this step is preferably carried out by introduction of pressurized clean steam into the first container and respectively into the second container, preferably in the high part of said container and respectively of the second container, and discharge of the condensates via the free end of the first pipe and respectively of the second pipe.

For each of the first container and the second container, the associated pipe thus advantageously fulfils a dual function, associated firstly with the sterilization of the inner volume of the container, as well as its own sterilization and that of the valves, and secondly with the transfer of the sterile product from one container to the other.

Similarly, in particularly preferred embodiments of the invention, the means for sealed connection arranged in the high part of the first container can also fulfil two functions, firstly for sterilization of the first container, and secondly for its filling with the sterile product.

In particular embodiments of the invention, the first pipe and/or the second pipe comprise(s) a drainage point between the associated distal valve and proximal valve.

The first pipe and/or the second pipe also preferably has/have a substantially uniform cross-section along their entire length.

The second container can be sterilized before the sterilization of the removable hose. In this case, at least one of the valves which are fitted on the second pipe associated with the second container is closed before implementation of the step d) of sterilization of the removable hose, and preferably the proximal valve. Thus, in particular embodiments of the invention, the step d) of sterilization of the inner volume of the removable hose is preceded by a step of closure of at least one valve associated with the second container, and preferably the proximal valve. This step of closure is preferably implemented before the step b) of sealed connection of the removable hose at the free end of the second pipe. Preferably, the two valves which are associated with the second container are closed before the connection of the removable hose with the second pipe, so as to make the device more secure in terms of sterility.

However the invention does not exclude the sterilization of the second container and the sterilization of the removable hose from being carried out simultaneously, for example by introduction of pressurized clean steam into the second container, preferably in the high part of the second container, and discharge of the condensates at the removable hose, at an end of the latter which is distant from the second container, with the distal valve and the proximal valve which are associated with the second container then both being open in order to allow the pressurized water steam to circulate from the second container, in all of the second pipe, and in the removable hose.

The device according to the invention preferably additionally comprises a board for rapid connection of the different component elements of the device, in particular of the first pipe and the first container, of the second pipe and the second container, and/or of the removable hose, to a sterilization system, in particular a system of the pressurized clean steam type.

Preferably, the valves which are fitted on the first pipe and/or the valves which are fitted on the second pipe are associated with means for automated control of their opening/closure. These means are also preferably configured so as to additionally control the sterilization system which is associated with the device.

The device and the transfer method according to the invention advantageously make it possible to transfer any type of sterile product, in particular high viscosity products, with high outputs of more than 15 kg/hour, by means of an adequate choice of diameter of the pipes and the connection hose.

This device is also entirely reusable, since it is sufficient to clean its component elements, and if applicable to re-sterilize the containers, in order to be able carry out a new transfer of sterile product. These cleaning and sterilization operations can advantageously be carried out in situ, at the place of transfer itself, for example by means of a clean steam sterilization system commonly used in sites for production and packaging of sterile products.

The device and the method according to the invention are inexpensive respectively in terms of purchasing and implementation.

The transfer can be carried out easily and rapidly, and furthermore in a so-called non-classified area, i.e. without environmental microbiological constraints, in compliance with the sterility standards imposed for the products.

According to another aspect, the present invention relates to a container containing a sterile product, i.e. a product which has been subjected to a sterilization treatment, and which, in particular according to the European pharmacopeia, has been subjected to a sterilization process, the sterilization value F0 of which is at least equal to 15 minutes. This container is equipped, preferably in its low part, with a pipe for emptying and/or filling, on which there are fitted in series two opening/closure valves which can be operated independently from one another. This pipe advantageously opens into a bottom wall of the container.

According to an advantageous characteristic of the invention, the two valves are closed, and the inner volume of the part of the pipe which is situated between the two valves is sterile, and thus constitutes a buffer area between the interior and the exterior of the container. The two valves advantageously form successive barriers against microbial contamination which can occur at the free end of the pipe situated opposite the container, thus protecting the sterile product which is contained in the container efficiently against any such contamination.

BRIEF DESCRIPTION OF THE DRAWINGS

The invention will now be described in greater detail within the context of preferred embodiments, which in no way limit it, represented in FIGS. 1 to 5, in which.

DETAILED DESCRIPTION OF THE EMBODIMENTS

Figure 1:
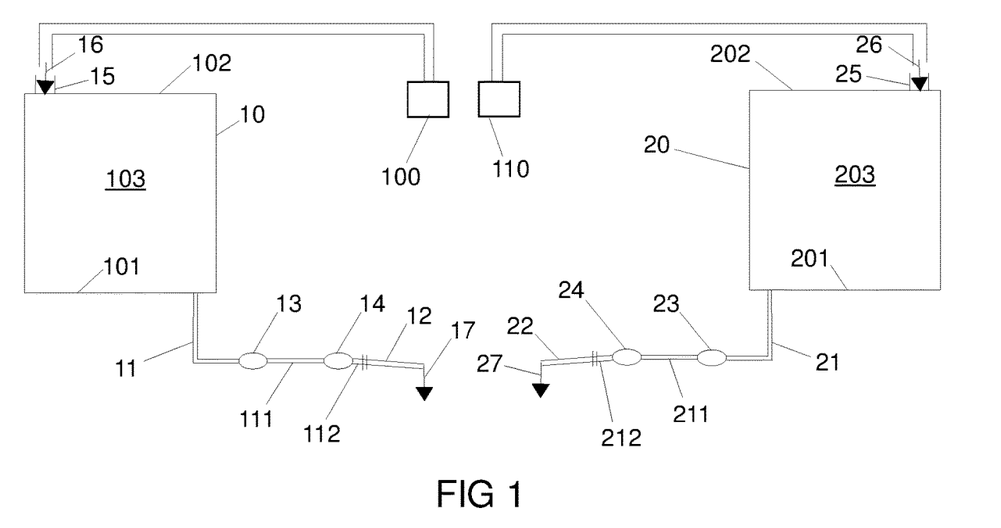
FIG. 1 represents schematically some of the component elements of a device according to an embodiment of the invention, in a configuration corresponding to a preliminary step of a method according to the invention for transferring a sterile product from a first container into a second container, said step consisting of the sterilization of the first container and the second container.

A device for transferring in aseptic conditions a sterile product from one container to another, according to a particular embodiment of the present invention, is represented schematically and partially in FIG. 1.

This device comprises a first container 10 and a second container 20. These containers can be of any type commonly used in lines for production/packaging of sterile products. They can in particular be vessels for storage and/or transfer of fluid sterile products, made of stainless metal. These vessels may or may not have the same form and the same inner volume.

According to the invention, the first container 10 is intended to contain the sterile product initially, and the second container 20 is intended to receive the sterile product after its transfer, on the understanding that these respective roles are interchangeable.

The first container 10 is equipped with a first pipe 11 which opens into its bottom wall 101. On this first pipe 11 there are fitted two valves for opening/closure of the pipe, which can be operated independently from one another: a so-called proximal valve 13, arranged on the first container 10 side, and a so-called distal valve 14, arranged on the side of the free end 112 of the first pipe 11 side opposite the first container 10.

The first pipe 11 preferably has a substantially constant cross-section along its entire length. Its part which is arranged between the proximal valve 13 and the distal valve 14 is called the interposed part 111.

In its high part for example, as illustrated in FIG. 1, at its upper wall 102, the first container 10 also comprises a second connector 15 for sealed connection to a system 100 for sterilization of its inner volume 103, for example to a clean steam generator device, and optionally to a filling hose. This means for connection is conventional in itself.

The second container 20 has characteristics similar to those previously described with reference to the first container 10: it is equipped with a second pipe 21 which opens into its bottom wall 201. On this second pipe 21 there are fitted two valves for opening/closure of the pipe, which can be operated independently from one another: a so-called proximal valve 23, which is arranged on the second container 20 side, and a so-called distal valve 24, which is arranged on the side of the free end 212 of the second pipe 21 opposite the second container 20.

The second pipe 21 preferably has a constant cross-section along its entire length. This cross-section can be substantially identical to that of the first pipe 11. Its part which is arranged between the proximal valve 23 and the distal valve 24 is called the interposed part 211.

In its high part, for example at its upper wall 202, the second container 20 also comprises a fourth connector 25 for sealed connection to a system 110 for sterilization of its inner volume 203, for example to a clean steam generator device. This means for connection is conventional in itself.

By convention, in the figures which are appended to the present description, the closure position of the valves will be illustrated by a cross formed on the valve, whereas the valves in the open position will be without a cross.

In a preliminary step of a method for transferring a sterile product between two containers according to an embodiment of the invention, which step is illustrated in FIG. 1, the first container 10 and the second container 20 are subjected to a sterilization treatment. These sterilization operations can be carried out simultaneously or successively, including at different times, in the same place or in different places, and by means of the same sterilization system or of different systems.

The sterilization is preferably carried out by means of pressurized clean steam, using a clean steam generator device which in itself is conventional.

For this purpose, for the first container 10 for example, the second connector 15 for connection which are arranged in the high part of the first container 10 are connected, for example via a coupling board provided for this purpose, to the sterilization system 100. The free end 112 of the first pipe 11 is connected by a hose 12 for recuperation of the condensates, to the same coupling board.

The two respectively proximal 13 and distal 14 valves are open, and pressurized clean steam is introduced into the first container 10 via the second connector 15 for sealed connection, as shown at 16 in FIG. 1. This clean steam fills the first container 10, and escapes via the first pipe 11, through the hose 12 for discharge of the condensates, as indicated at 17 in FIG. 1. This processing step is implemented for a length of time sufficient to ensure that a satisfactory level of sterility is obtained of the inner volume 103 of the first container 10, the first pipe 11 and the associated proximal 13 and distal 14 valves.

Upon completion of this step, at least one of these valves 13, 14 is closed. Preferably, the proximal valve 13 and the distal valve 14 are both closed, such as to ensure that the interposed part 111 of the first pipe is empty and sterile, thus constituting a buffer area between the exterior and the interior of the first container 10.

The second connector 15 for connection of the first container 10 to the sterilization system are disconnected.

The sterilization operations can be carried out in a similar manner for the second container 20, the pressurized clean steam being introduced into the second container 20 by the fourth connector 25 for sealed connection, as indicated at 26 in FIG. 1, and the condensates being discharged from the second pipe 21 via a discharge hose 22, according to the direction indicated at 27.

Figure 2:
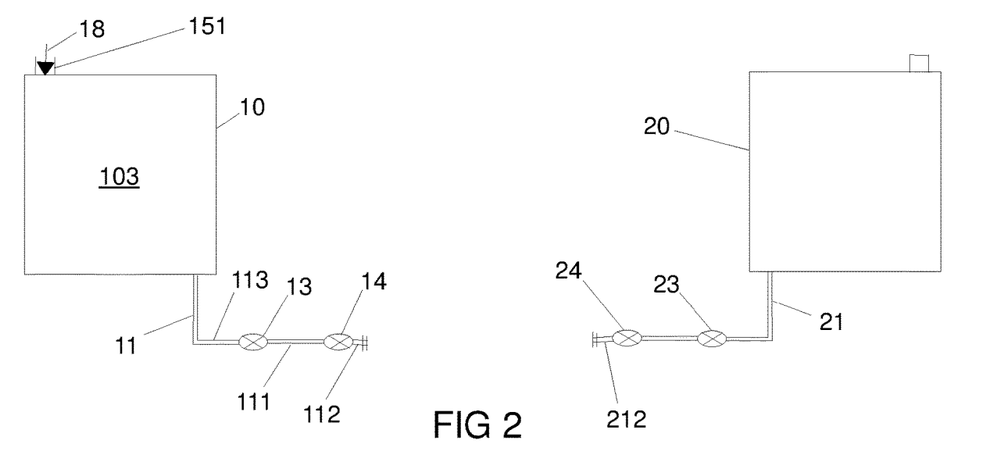
FIG. 2 shows the device of FIG. 1, in a configuration upon completion of said preliminary step.

The device upon completion of this preliminary step is represented schematically in FIG. 2. The first container 10 and the second container 20 have been disconnected from the sterilization system(s). All the valves are closed, and the inner volumes of the first container 103 and the second container 203, as well as of the first pipe 11 and the second pipe 21, are sterile.

The interposed parts 111, 211 respectively of the first pipe 11 and the second pipe 21 advantageously constitute buffer areas which protect the inner volumes respectively of the first container 103 and the second container 203 against any microbiological contamination.

Once it is sterile, the first container 10 is filled with the sterile product to be transferred. For this purpose, it is connected by means of the third connector 151 for sealed connection to a filling hose, not represented in the figure. The third connector 151 for sealed connection to the filling hose may be same as the second connector 15 for sealed connection to the system 100 for sterilization of the inner volume 103 of the first container 10. The sterile product is thus introduced into the first container 10, as indicated at 18 in FIG. 2. It fills at least partly the inner volume 103 of the container, as well as, by means of a phenomenon of gravity, the part of the first pipe 11 which is arranged between the first container 10 and the associated proximal valve 13, known as the proximal part 113. The interposed part 111 of the first pipe 11 advantageously remains empty and sterile.

Figure 3:
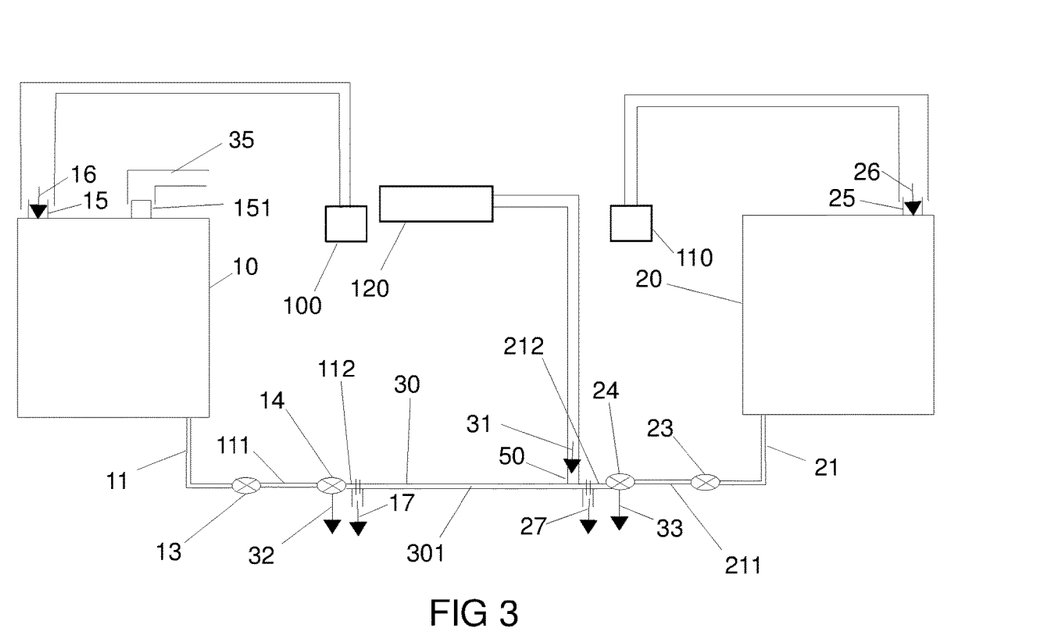
FIG. 3 shows the device of FIG. 1, in a configuration corresponding to a subsequent step of the transfer method according to the invention, consisting of the sterilization of a removable hose which connects the first pipe and the second pipe.

The following step of a transfer method according to the invention is illustrated in FIG. 3.

The device comprises a removable hose 30 for sealed connection of the free end 112 of the first pipe 11 and of the free end 212 of the second pipe 21. This hose, which initially is not sterile, is put into place in order to ensure this sealed connection. It preferably has a constant cross-section along its entire length. This cross-section is preferably substantially identical that to that of the first pipe 11 and to that of the second pipe 21.

The device additionally comprises a connector 50 for connection of the removable hose 30 to a sterilization system 120, which is conventional in itself, and is preferably identical to, or at least the same type as, the one implemented for the sterilization of the first container 10 and/or of the second container 20. Preferably, it is a pressurized clean steam sterilization system.

The connector 50 can be of any type which in itself is conventional, and they can be operated such as to permit sterilization of the inner volume 301 of the removable hose 30, when the latter connects the first pipe 11 and the second pipe 21.

They are configured such as to ensure introduction of pressurized clean steam into a first end part of the removable hose 30, as shown at 31 in FIG. 3, and discharge of the condensates at an opposite end part, for example, but without limitation to this, as indicated at 32 in FIG. 3, at the distal valve 14 which is associated with the first pipe 11, via a third channel which this valve comprises for this purpose. Part of the condensates can also be discharged at the distal valve 24 which is associated with the second pipe 21, as indicated at 33 in FIG. 3, so as to ensure that all of the inner volume 301 of the removable hose 30 and of the respective free ends of the first pipe 11 and of the second pipe 21 are sterilized, as far as the distal valves 14, 24. This sterilization treatment is continued until an adequate level of sterility is obtained.

During this sterilization operation, the interposed part 111 of the first pipe 11 advantageously protects the sterile product contained in the first container 10 and in the proximal part 113 of the first pipe 11 against the heat of the sterilization steam.

As far as the second container 20 is concerned, during this operation, the distal valve 24 can be open, so as to permit a new sterilization treatment of the interposed part 211 of the second pipe 21. This distal valve 24 is preferably closed. In this last case, the associated proximal valve 23 can equally well be closed or open. Preferably, the proximal valve 23 and the distal valve 24 are both closed, so as to ensure that sterile conditions are maintained in the second container 20.

Upon completion of this step, all of the first container 10, the first pipe 11, the removable hose 30, the second pipe 21 and the second container 20, i.e. all of the path to be followed by the sterile product for its transfer from the first container 10 to the second container 20, are sterile.

Figure 4:
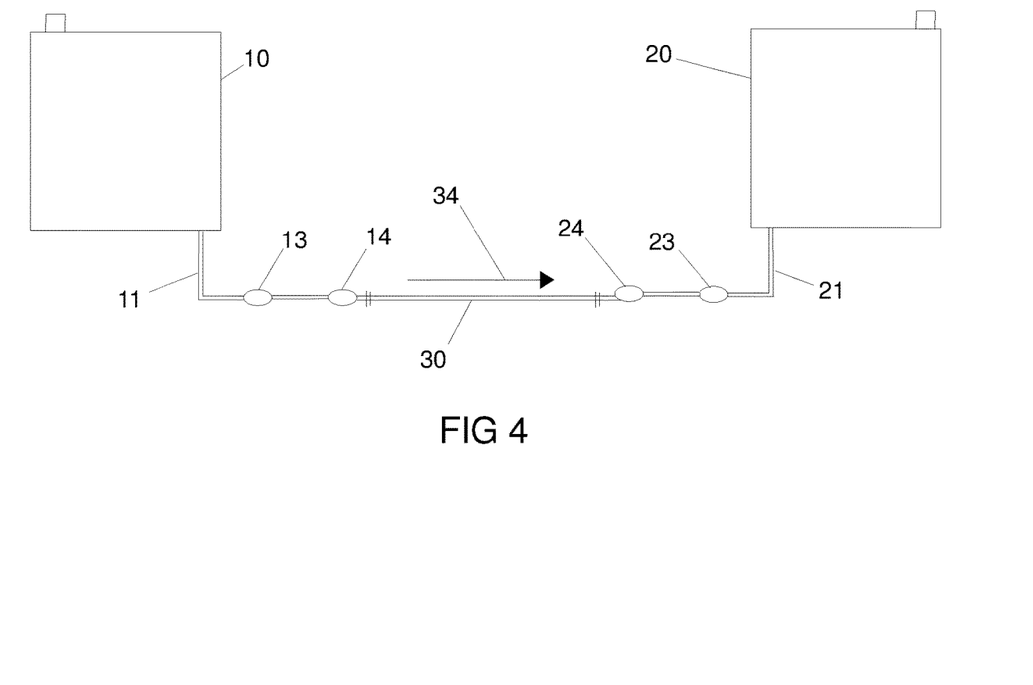
FIG. 4 shows the device of FIG. 3, in a further subsequent step of the transfer method according to the invention, during which the sterile product is transferred from the first container to the second container.

The following step, which constitutes the actual transfer, is illustrated schematically in FIG. 4.

All of the valves, more particularly the proximal valve 13 and the distal valve 14 which are associated with the first container 10, and the proximal valve 23 and the distal valve 24 which are associated with the second container 20, are opened, in order to put into effect the transfer of the sterile product from the first container 10 to the second container 20, by means of the first pipe 11, the removable hose 30, then the second pipe 21, as indicated at 34 in FIG. 4. This transfer is advantageously carried out in aseptic conditions, preserving the sterility of the product transferred, without needing to ensure microbiological control of the environment of the containers. It makes it possible to transfer any type of product easily and rapidly, including products with a high level of viscosity, and moreover at the required flow rate, which is made possible in particular by an appropriate choice of the inner diameter of the first pipe 11, the second pipe 21 and the removable hose 30.

When the transfer of the sterile product into the second container 20 is completed, the distal valve 24 and the proximal valve 23 fitted on the second pipe 21 are closed, such as to isolate the inner volume 203 of the second container 20 which contains the sterile product from the external environment.

If all of the sterile product initially contained in the first container 10 has not been transferred into the second container 20, the distal valve 14 and the proximal valve 13 fitted on the first pipe 11 are also closed, so as to isolate the inner volume 103 of the first container 10 which still contains sterile product from the external environment.

Figure 5:
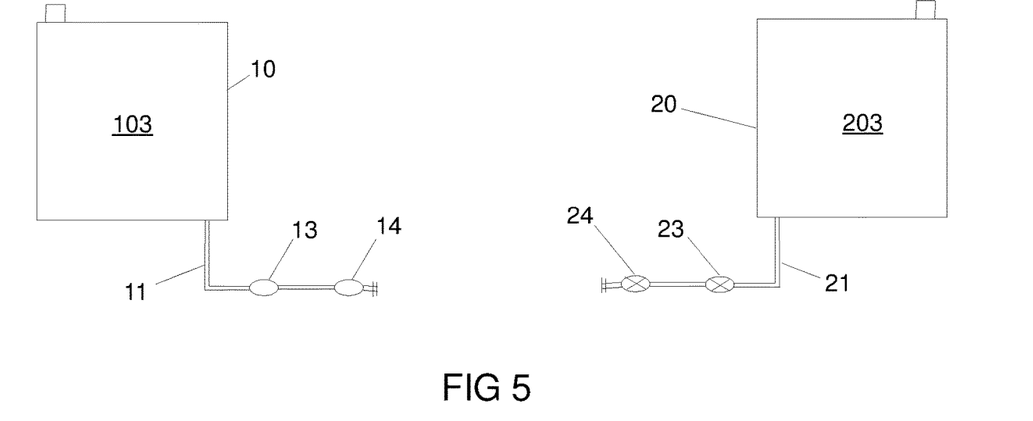
FIG. 5 illustrates the device of FIG. 4 upon completion of implementation of a transfer method according to the invention.

The removable hose 30 is then disconnected from the second pipe 21, as well as from the first pipe 11, in order to obtain the device in its configuration represented schematically in FIG. 5.

When they are empty, the removable hose 30, as well as the first container 10 and the first pipe 11, can easily be cleaned, in particular on the spot, in order to be reused for another subsequent transfer operation.

The second container 20 which contains the sterile product can advantageously be used for transfer of the sterile product in aseptic conditions into a third container, in particular by implementation of the method according to the invention, for example such as previously described. For this purpose, the second container 20 then plays the role of a first container, which is advantageously permitted by the fact that it has characteristics similar to those of the first container according to the invention. The method described above can then be applied once more, with the exception of the steps of sterilization and filling of the first container, which no longer need to be carried out.

The invention claimed is:

1. A device for transferring a sterile product in aseptic conditions from a first container into a second container, comprising:
    a first container containing said sterile product and equipped with an outlet comprising a first pipe on which there are fitted in series two opening/closure valves which can be operated independently from one another, a first or proximal valve is arranged on a first container side of the first pipe and a second or distal valve is arranged on an opposite free end side of the first pipe, at least one of said first valve and said second valve being closed;
    a second container equipped with an inlet comprising a second pipe on which there are fitted in series two opening/closure valves which can be operated independently from one another, a first or proximal valve is arranged on a second container side of the second pipe and a second or distal valve is arranged on an opposite free end side of the second pipe, the second container is distinct and independent of the first container, the first and second containers do not share any interface with each other;
    a hose removably connected in a sealed manner to the free end side of the first pipe and to the free end side of the second pipe; and
    a connector to connect the hose to a first sterilization system, said connector configured to enable a sterilization of an inner volume of the hose by the first sterilization system while said hose is connected to the first pipe and the second pipe.

2. The device as claimed in claim 1, wherein the first container comprises a second connector to provide a sealed connection to a second sterilization system to sterilize an inner volume of the first container.

3. The device as claimed in claim 2, wherein the second connector providing the sealed connection of the first container to the second sterilization system is distinct from the first pipe.

4. The device as claimed in claim 1, wherein the first container comprises a third connector to provide a sealed connection to a filling hose.

5. The device as claimed in claim 1, wherein the second container comprises a fourth connector to provide a sealed connection to a third sterilization system to sterilize an inner volume of the second container.

6. The device as claimed in claim 5, wherein the fourth connector providing the sealed connection of the second container to the third sterilization system is distinct from the second pipe.

7. The device as claimed in claim 4, wherein the first container comprises a second connector to provide a sealed connection to a second sterilization system to sterilize an inner volume of the first container; and wherein the third connector providing the sealed connection to the filling hose coincides with said second connector providing the sealed connection to the second sterilization system.

8. A method for transferring a sterile product in aseptic conditions from a first container into a second container,
wherein the first container is equipped with an outlet comprising a first pipe on which there are fitted in series two opening/closure valves which can be operated independently from one another, a first or proximal valve is arranged on a first container side of the first pipe and a second or distal valve is arranged on an opposite free end side of the first pipe;
wherein the second container is equipped with an inlet comprising a second pipe on which there are fitted in series two opening/closure valves which can be operated independently from one another, a first or proximal valve is arranged on a second container side of the second pipe and a second or distal valve is arranged on an opposite free end side of the second pipe;
the method comprises:
filling the first container with the sterile product in a configuration in which both valves associated with the first container are closed, and
closing both valves associated with the second container;
the method then comprises the successive steps of:
connecting the free end of the first pipe and the free end of the second pipe by a removable hose to provide a sealed connection;
connecting the removable hose, connected to the first pipe and the second pipe, to a sterilization system using a connector;
sterilizing an inner volume of the removable hose by the sterilization system;
disconnecting the removable hose from the sterilization system;
opening of all of the valves associated respectively with the first container and the second container;
transferring the sterile product from the first container into the second container via the removable hose; and
closing at least one valve associated with the second container.

9. The method as claimed in claim 8, wherein the sterilizing step is performed by a pressurized clean steam.

10. The method as claimed in claim 8, further comprising a preliminary step of sterilizing an inner volume of the second container.

11. The method as claimed in claim 8, further comprising a preliminary step of sterilizing an inner volume of the first container.

12. The method as claimed in claim 10, wherein the sterilization of the inner volume of the second container is performed by a pressurized clean steam.

13. The method as claimed in claim 12, wherein the sterilization of the inner volume of the second container is performed by introduction of the pressurized clean steam into the second container and discharge of condensates via the free end of the second pipe.

14. The method as claimed in claim 12, wherein the sterilization of the inner volume of the second container and the sterilization of the inner volume of the removable hose are performed by the same sterilization system.

15. The method as claimed in claim 11, wherein the sterilization of the inner volume of the first container is performed by a pressurized clean steam.

16. The method as claimed in claim 15, wherein the sterilization of the inner volume of the first container is performed by introduction of the pressurized clean steam into the first container and discharge of condensates via the free end of the first pipe.

17. The method as claimed in claim 15, wherein the sterilization of the inner volume of the first container and the sterilization of the inner volume of the removable hose are performed by the same sterilization system.

* * * * *